US00PP11518P

United States Patent [19]

Carruth

[11] Patent Number: Plant 11,518

[45] Date of Patent: Sep. 26, 2000

[54] CLIMBING ROSE PLANT NAMED 'WEKROALT'

[75] Inventor: Thomas F. Carruth, Altadena, Calif.

[73] Assignee: Weeks Wholesale Rose Grower, Inc., Upland, Calif.

[21] Appl. No.: 09/198,969

[22] Filed: Nov. 23, 1998

[51] Int. Cl.[7] ..... A01H 5/00

[52] U.S. Cl. ..... Plt./109

[58] Field of Search ..... Plt./102, 109, 141, Plt./142, 143

*Primary Examiner*—Howard J. Locker

*Attorney, Agent, or Firm*—Christie, Parker & Hale, LLP

[57] ABSTRACT

A new variety of climbing rose suitable for garden decoration, having flowers of irregularly striped and flecked red and white coloration.

1 Drawing Sheet

BACKGROUND OF THE INVENTION

This invention relates to a new and distinct variety of Climbing Rose. The varietal denomination of the new variety is 'WEKroalt'. It has as its seed parent the variety known as 'MACminmo' (U.S. Plant Pat. No. 7,319) and as its pollen parent the variety known as 'DELmur'.

SUMMARY OF THE INVENTION

Among the features which distinguish the new variety from other presently available and known commercial rose cultivars are the following combination of characteristics: its blushed coloration on the buds, its clusters of large flowers with irregularly striped red and white coloration, its abundance of large semi-glossy foliage and its very vigorous growth. The plant is a spreading climbing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKroalt' may be asexually propagated by cuttings, budding or grafting.

COMPARISON WITH PARENTS

The new rose may be distinguished from its seed parent, 'MACminmo' by the following combination of characteristics: whereas 'WEKroalt' bears large flowers, the flowers of 'MACminmo' are significantly smaller. The seed parent bears small foliage, whereas the new seedling has significantly larger foliage. 'MACminmo' is classified as a shrub with a spreading mature habit, whereas 'WEKroalt' is classified as a climbing rose with a significantly larger and more spreading mature habit.

The new variety may be distinguished from its pollen parent, 'DELmur' by the following combination of characteristics: whereas 'WEKroalt' bears clusters of flowers with an irregular striping of red and white coloration, 'DELmur' bears flowers of a solid red coloration with significantly less clusters. The foliage of the pollen parent has a matte finish, whereas the foliage of the new variety is significantly more glossy in finish.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

FLOWER

The new variety usually bears its flowers in clusters of four to five or more per stem. Flowers are borne in irregular rounded clusters on normal strong medium to long stems (about 20 to about 30 cms.). Outdoors, the plant blooms very abundantly and nearly continuously during the growing season. The flowers have a moderately strong apple-like to spicy fragrance.

BUD

The peduncle is about 5 to about 6.5 cms. in length, of average caliper, and usually erect. It is moderately smooth with some stipitate glands and few hairs. Peduncle color is between 144A and 139B sometimes moderately suffused with between 183C and 183B.

Before the calyx breaks, the bud is about 1.4 to about 1.8 cms. in diameter at the widest point, about 2.3 to about 3 cms. in length, and pointed to ovoid in shape. The surface of the bud bears numerous stipitate glands and some hairs, usually with slender entire foliaceous parts extending beyond the tip of the bud about ½ or more of its length. Bud color is between 144A and 139B often moderately suffused with between 183C and 183B.

The inner surface of the sepals is lined and edged with very fine wooly tomentum; sepal margins are lined with a few stipitate glands and hairs.

As the petals open (after the calyx breaks), the bud is about 1.8 to about 2.2 cms. in diameter at the widest point, about 2 to about 3 cms. in length, and very pointed to urn-shaped in form. The color of the under surfaces of the newly opened petals is irregularly striped and flecked with as dark as between 53A and 46A to as light as between 155D and 155B. The White pigmented areas of the under surface of the newly opened petal often blush to between 63C and 54B. At the point where the petal attaches, there is a moderately large zone of between 8B and 13C. The color of the upper surfaces of the newly opened petals is of similar hues but of different marking to the under surface of the newly opened petals. There is little to no blush color of the white pigmented areas on the inner surface of the newly opened petals. At the point where the petal attaches, there is a moderately large zone of between 8A and 13B.

BLOOM

When fully open, the bloom ranges from about 8 to about 10 cms. in diameter. Petalage is single to semi-double with about 8 to 12 petals usually with about 1 to 2 petaloids arranged irregularly. When partially open, the bloom form is very high centered and the petals are somewhat loosely spiraled with petal edges very slightly reflexed outward. When fully open, the bloom form is somewhat flat and the petals are moderately flat to undulated with petal edges very slightly reflexed outward.

PETALS

The substance of the petals is moderately heavy and of medium to thick thickness, with upper surfaces moderately velvety to slightly satiny and under surfaces mostly satiny to somewhat shiny. The petals are nearly round to very broadly obovate in shape usually with rounded apices, sometimes notched with one to two notches.

NEWLY OPENED FLOWER

The under surface of the petals is irregularly striped and flecked with as dark as between 53A and 46A to as light as between 155D and 155B. The white pigmented areas of the under surface of the newly opened petal often blush to as dark as between 63C and 54B. At the point where the petal attaches, there is a moderately large zone of between 8B and 13C.

The upper surface of the petals is of similar hues but of different marking to the under surface. The white pigmented areas on the outer half of the upper surfaces often blush to between 63C and 68B. At the point where the petal attaches, there is a moderately large zone of between 8A and 13B.

The general tonality of the newly opened flower is irregularly striped and flecked with as dark as between 53A and 46A to as light as between 155D and 155B. The outer portions of the white pigmented areas often blush to between 63C and 68B. The center of the flower is between 8A and 13B.

THREE DAY OLD FLOWER

The under surface of the petals is irregularly striped and flecked with as dark as between 59B and 53A to as light as between 56D and 155B. The lighter pigmented areas of the under surface of the newly opened petal often blush to between 59C and 63B. At the point where the petal attaches, there is a moderately large zone of between 4D and 155A.

The upper surface of the petals is irregularly striped and flecked with as dark as between 60A and 53A to as light as between 56D and 155B. The white pigmented areas on the outer half of the upper surfaces often blush to between 63B and 68A. At the point where the petal attaches, there is a moderately large zone of between 4D and 8D. The marking on the upper surface differs from the marking on the under surface of each petal.

The general tonality of the three day old flower is irregularly striped and flecked with as dark as between 60A and 53A to as light as between 56D and 155B. The white pigmented areas on the outer half of the upper surfaces often blush to between 63B and 68A. The center of the flower is between 4D and 8D. On the spent bloom, the petals usually drop off cleanly.

In September in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (approximately 100) and are arranged regularly about the pistils. The filaments are medium to long in length, most with anthers. Filaments are near 13B in color, sometimes moderately suffused with near 46C. The anthers are medium sized opening approximately at the same time. Anther color is between 13A and 16A when immature and between 163A and 165A at maturity. Pollen is moderate to abundant and near 13B in color.

FEMALE REPRODUCTIVE ORGANS

Pistils vary in number (approximately 45). The styles are moderately uneven, short to average in length, somewhat thin in caliper, and moderately bunched. Stigma color is between 8D and 9D. Style color is near 46D. Ovaries are usually all enclosed in the calyx.

Hips are of average length, moderately ovoid to globular in form and between 28A and 33A in color when ripe. The hip surface is moderately smooth with thick fleshy walls. The sepals usually persist. There are approximately 7 to 11 seeds of medium size.

FOLIAGE

The compound leaves are usually comprised of three to seven leaflets and are borne very abundantly. The leaves are about 9.5 to about 12.5 cms. in length and about 8 to about 10.5 cms. in width at the widest point, moderately heavy in texture, and semi- glossy to moderately rugose in finish. The leaflets are about 5.5 to about 7 cms. in length and about 3 to about 4 cms. in width at the widest point, shaped moderately oval to somewhat ovate with acute to somewhat acuminate apices and rounded bases. Their margins are usually serrate.

The upper surface of the mature leaf is between 147A and 139A. The under surface of the mature leaf is between 147B and 139C. The upper surface of the young leaf is between 147A and 139B, sometimes very lightly suffused with between 183B and 187C. The under surface of the young leaf is between 147B and 139C, often moderately suffused with between 183B and 187C.

The rachis is average in caliper and moderately smooth. The upper side is moderately grooved with some stipitate glands and hairs on the edges of the grooves. The under side of the rachis is somewhat rough with few stipitate glands and about 1 to about 4 very small prickles.

The stipules are about 1.1 to about 1.5 cms. in length with moderately narrow medium to long straight points that usually turn out at an angle of more than 45 degrees.

The plant displays an above average degree of resistance to powdery mildew and blackspot as compared to other commercial varieties grown under comparable conditions in Upland, Calif.

GROWTH

The plant has a spreading moderately long growth habit with canes of about 250 to about 360 cms. in length and with very full branching. It displays very vigorous growth and the canes are of medium to heavy caliper for the class.

The color of the major stems is near 148A. They bear several large prickles which are about 0.9 to about 1.3 cms. in length. The large prickles are almost straight angled moderately downward with a somewhat narrow moderately long base; prickle color is between 164A and 165A. The major stem bears a few small prickles of similar shape and coloration.

The color of the branches is between 144A and 139B, sometimes lightly blushed on the side exposed the sun with between 183B and 187B. They bear several large prickles, which are of similar size and shape to the large prickles on the major stems; prickle color is between 164B and 161A, often lightly suffused with between 184B and 181A. The branches bear a few small prickles of similar shape and coloration.

The color of the new shoots is between 144A and 139C often heavily blushed on the side exposed to the sun with between 183A and 187A. They bear several large prickles, which are of similar size and shape to the large prickles on the major stems; prickle color is between 183A and 187A. The shoots bear a few small prickles of similar shape and coloration.

I claim:

1. A new and distinct Climbing rose plant of the variety substantially as described and illustrated herein.

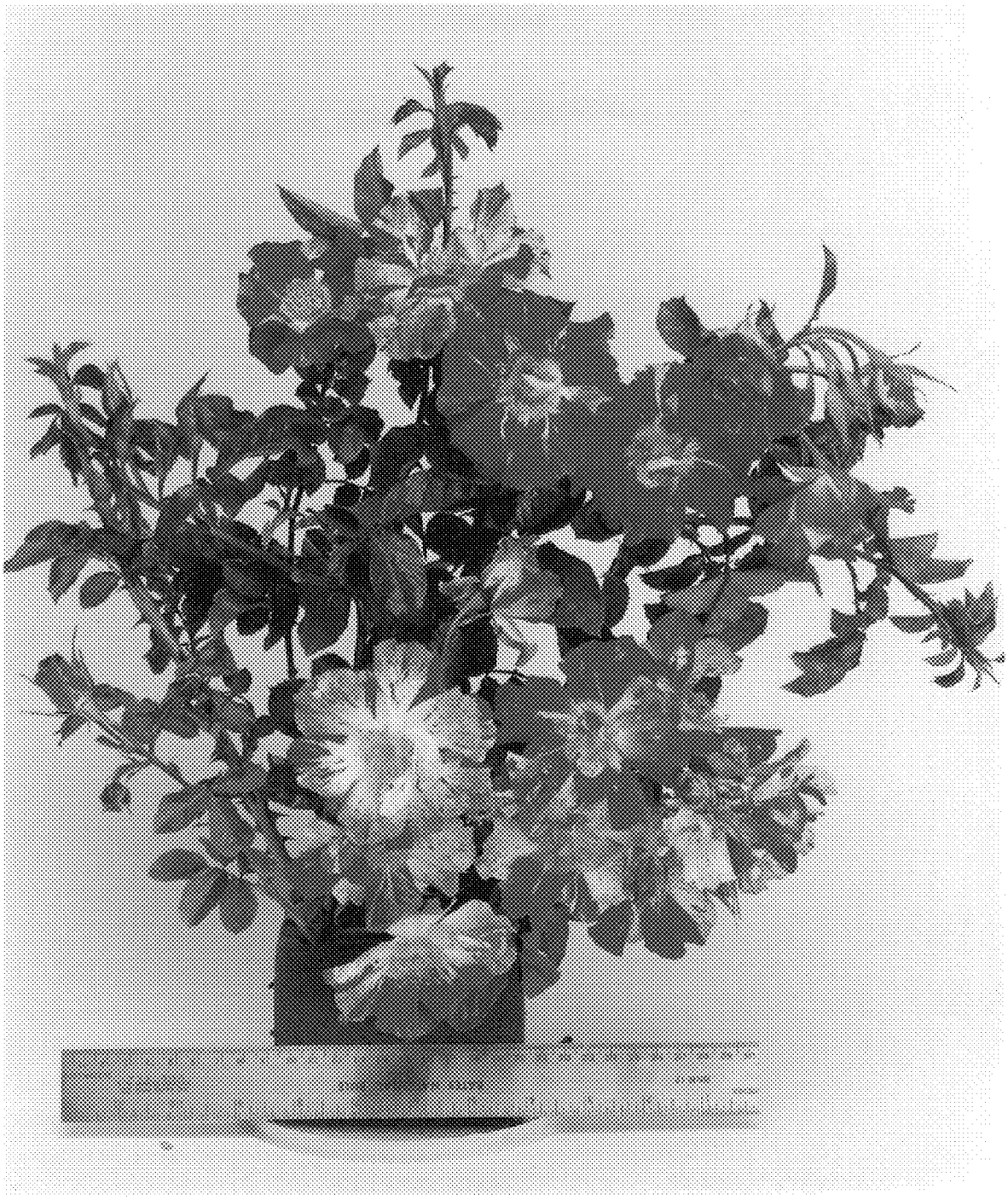

* * * * *